(12) United States Patent
Cardoso et al.

(10) Patent No.: US 10,407,518 B2
(45) Date of Patent: *Sep. 10, 2019

(54) CATALYST SUPPORT AND RELATED PROCESSES

(71) Applicant: Braskem S.A., Camacari, BA (BR)

(72) Inventors: Renata da Silva Cardoso, Sao Paulo (BR); Jonas Alves Fernandes, Sao Paulo (BR); Marcia Regina Washburger, Sao Paulo (BR); Cesar Augusto Sales Barbosa, Sao Paulo (BR)

(73) Assignee: Braskem S.A., Camacari, BA (BR)

( * ) Notice: Subject to any disclaimer, the term of this patent is extended or adjusted under 35 U.S.C. 154(b) by 0 days.

This patent is subject to a terminal disclaimer.

(21) Appl. No.: 15/836,032

(22) Filed: Dec. 8, 2017

(65) Prior Publication Data

US 2018/0155458 A1 Jun. 7, 2018

Related U.S. Application Data

(63) Continuation-in-part of application No. 15/105,788, filed as application No. PCT/BR2014/050048 on Dec. 17, 2014, now Pat. No. 9,873,750.

(Continued)

(51) Int. Cl.
| | |
|---|---|
| *C08F 4/02* | (2006.01) |
| *B01J 35/00* | (2006.01) |
| *B01J 35/08* | (2006.01) |
| *B01J 37/00* | (2006.01) |
| *B01J 37/06* | (2006.01) |

(Continued)

(52) U.S. Cl.
CPC ............ *C08F 4/02* (2013.01); *B01J 35/0006* (2013.01); *B01J 35/08* (2013.01); *B01J 37/0072* (2013.01); *B01J 37/06* (2013.01); *C07C 19/08* (2013.01); *C07C 21/18* (2013.01); *C07C 31/202* (2013.01); *C08L 23/02* (2013.01); *C08L 67/04* (2013.01);

(Continued)

(58) Field of Classification Search
CPC ..... C08F 4/02; C08F 2410/01; B01J 35/0006; C07C 21/18; C07C 19/08
See application file for complete search history.

(56) References Cited

U.S. PATENT DOCUMENTS

| | | | | |
|---|---|---|---|---|
| 5,100,849 A * | 3/1992 | Miya | ................... | C08F 10/00 269/125 |
| 7,060,763 B2 * | 6/2006 | Evangelisti | ............. | C07F 3/003 502/103 |

(Continued)

*Primary Examiner* — Catherine S Branch
(74) *Attorney, Agent, or Firm* — Duane Morris LLP

(57) ABSTRACT

The present invention describes a catalyst support, which is used as an inorganic carrier for a Ziegler-Nata catalyst (ZN), using a modified spray cooling method. Such a catalyst support is prepared from alcoholic solutions of (a) an inorganic compound, in which the inorganic compound is a magnesium compound and (b) an inorganic compound and one or more additives. The solutions are prepared at a temperature below 100° C., carried through a nozzle placed inside a reactor, and sprayed into droplets forming a solid precipitate, which is generally spherical, when in contact with an inert hydrocarbon solvent at low temperature. The obtained catalyst support is reacted with a titanium compound, preferably titanium tetrachloride, in order to produce an active catalyst for olefin polymerization.

7 Claims, 5 Drawing Sheets

Illustration of the apparatus used to prepare catalytic support. (1) reactor A; (2) transfer line; (3) jacketed system for heating control; (4) liquid pressure; (5) gas pressure; (6) atomizer / nozzle; (7) reactor B.

Related U.S. Application Data

(60) Provisional application No. 61/917,764, filed on Dec. 18, 2013.

(51) Int. Cl.
*C08L 23/02* (2006.01)
*C08L 67/04* (2006.01)
*C07C 19/08* (2006.01)
*C07C 21/08* (2006.01)
*C07C 31/20* (2006.01)
*C07C 21/18* (2006.01)

(52) U.S. Cl.
CPC ....... *C08F 2410/01* (2013.01); *C08L 2314/02* (2013.01)

(56) References Cited

U.S. PATENT DOCUMENTS

| | | | |
|---|---|---|---|
| 2012/0130034 A1* | 5/2012 | Yang | B01J 31/069 526/203 |
| 2012/0264590 A1* | 10/2012 | Li | C08F 10/00 502/8 |

\* cited by examiner

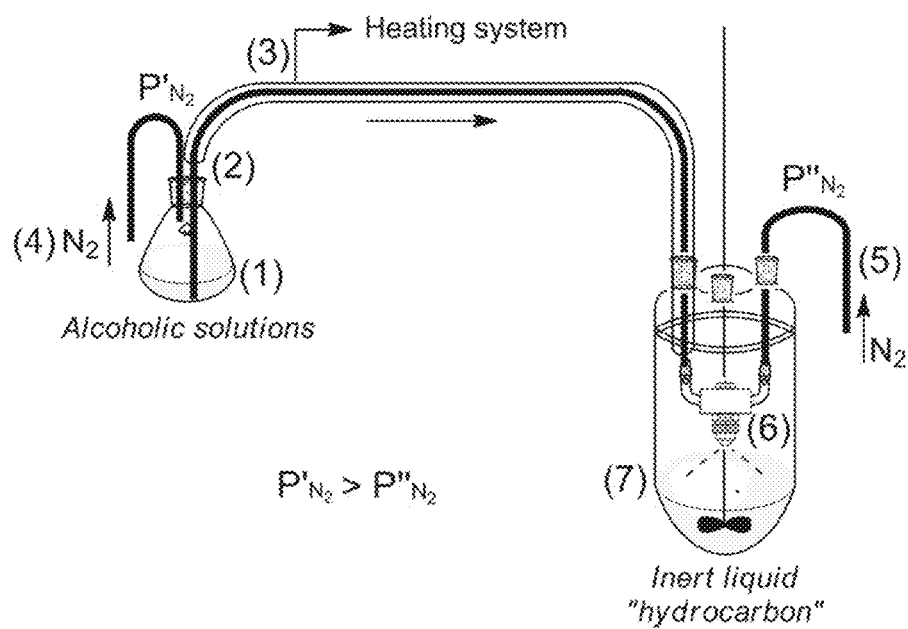
Figure 1 – Illustration of the apparatus used to prepare catalytic support. (1) reactor A; (2) transfer line; (3) jacketed system for heating control; (4) liquid pressure; (5) gas pressure; (6) atomizer / nozzle; (7) reactor B.

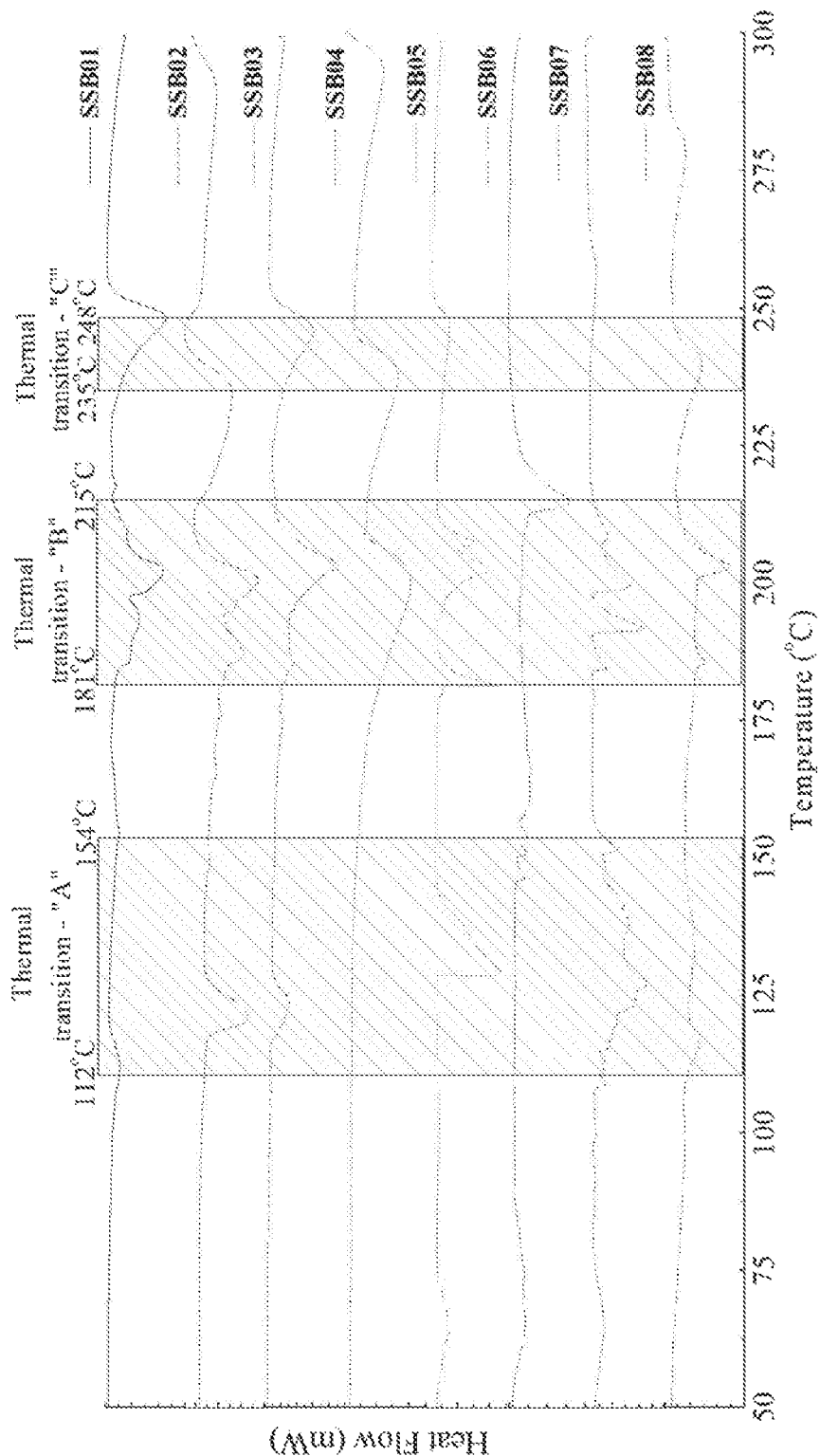
Figure 2 - DSC thermogram of the supports SSB01 to SSB08.

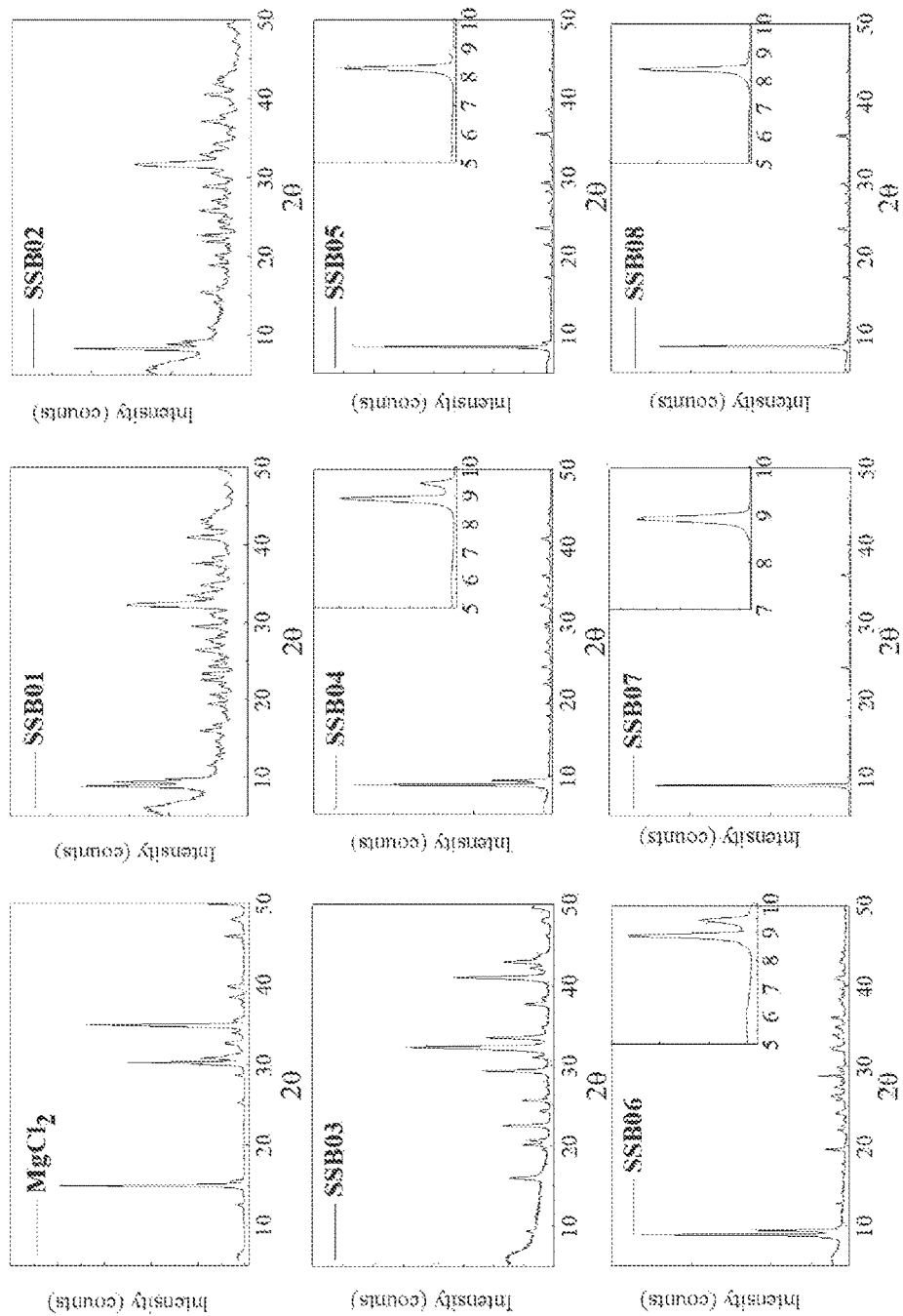
Figure 3 - Powder X-ray diffraction patterns of $MgCl_2$ and support samples SSB01 to SSB08.

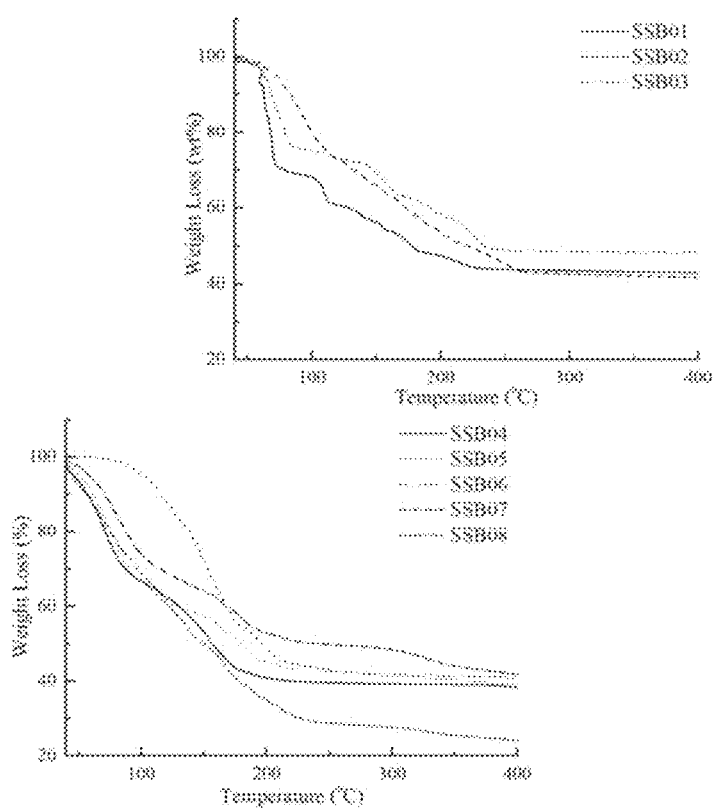
Figure 4 – Thermogravimetric analysis (TGA) of support samples SSB01 to SSB08.

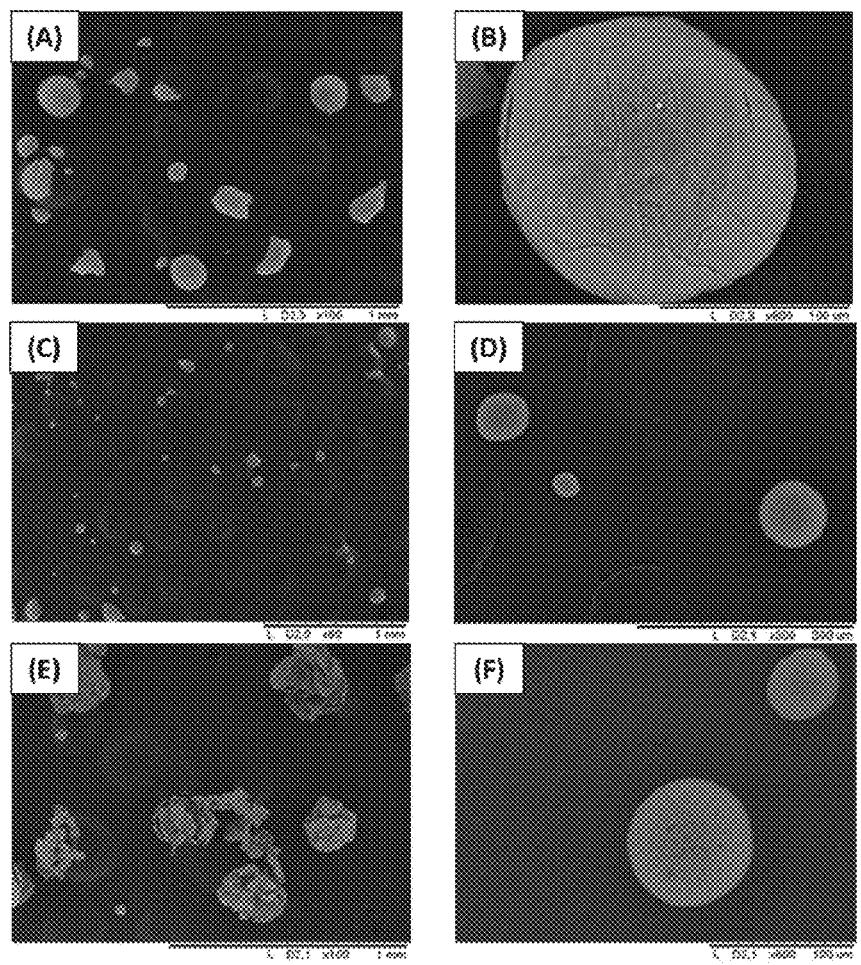
Figure 5 – Images obtained by Scanning Electron Microscope (SEM) of samples SSB01 (A) and (B); SSB02 (C) and (D); SSB03 (E) and (F).

CATALYST SUPPORT AND RELATED PROCESSES

CROSS-REFERENCE TO RELATED APPLICATIONS

This application is a continuation-in-part of U.S. Ser. No. 15/105,788, filed Jun. 17, 2016.

BACKGROUND OF THE INVENTION

Catalytic supports based on magnesium compounds, particularly magnesium chloride ($MgCl_2$), are the most effective for the production of Ziegler-Natta (ZN) catalysts for olefin polymerization. Perhaps one of the main advantages to use an inorganic carrier for a ZN catalyst is the control of the morphology, which enables the production of polymer with predictable shape, bulk density and particle size distribution due to the replica phenomenon. Given the importance of the support nature and its crystallization, it is important to explore alternatives routes for support preparation.

Since the early 1970s, the patent literature and scientific articles have described routes to prepare spherical support from magnesium halides. One of the most important and widely used routes to obtain spherical and porous particles is by oil emulsion. This method is described, for example, in the U.S. Pat. Nos. 4,469,648, 4,399,054, 5,578,541, and 6,861,385. Such documents describe a catalyst obtained from a support based on the formation of an emulsion of a fused product between $MgCl_2$ and alcohol at high temperature (120° C.) and pressure (9.8 bar) followed by subsequent precipitation of this emulsion in a non-solvent medium at low temperature. Furthermore, U.S. Pat. No. 6,323,152 teaches that a long contact period (longer than 10 hours) is required for a complete melting between the mixture components in oil ($MgCl_2$ and alcohol).

In another approach, spherical particles are obtained through a Spray-Drying technique, as mentioned in U.S. Pat. No. 6,982,237, EP0123767, U.S. Pat. Nos. 4,376,062, and 4,311,817. In this case, the solution is fed to the equipment by pumping and passing it through an atomizer at high temperature. The solvent evaporates in a chamber to form spherical dried particles. The product is separated in the cyclone from the gas and it is collected in a vessel followed by a solvent recovering step from the upper part of the cyclone. However, in this process it is necessary to control several parameters, for example; feeding rate, gas flow to spray, temperature of gas flow to spray, flow rate of carrier gas in a chamber, and temperature of carrier gas. Additionally, this process involves evaporation of the solvent for subsequent precipitation of the solid, which contributes to the particle formation. Thus, this technique is highly dependent on experimental conditions. For example, rapid removal of alcohol can lead to formation of fragile hollow particles, which are not suitable for the production of ZN catalysts due to the poor mechanical strength of the particles.

On the other hand, U.S. Pat. No. 4,421,674 describes catalyst supports which are obtained through a similar Spray-Drying technique. It describes the application of a solution of $MgCl_2$ with alcohol, which is heated from 40 to 100° C. This solution is then dispersed through a spray nozzle and the solvent evaporates at high temperature, approximately 180° C. In this case, a large amount of solvent is carried into the Spray-Dryer, reducing the holding capacity of the solvent (vapor) in the gas stream and which may result in high content of the solvent in the final product. It is worth noting that limited information was given concerning the support morphology in U.S. Pat. No. 4,421,674, and the catalyst obtained was evaluated only for ethylene polymerization carried out at low pressure.

Another route to spherical support production is through a Spray-Cooling technique, as mentioned in U.S. Pat. No. 4,829,034. A solution, suspension or melted product is atomized into a spray of fine droplets of spherical shape inside a spray cooling chamber. In this case the droplets meet the inert gas stream at low temperature, which solidifies the droplets. A mixture of magnesium compound, alcohol, and internal electron donor in molten state is then pumped to a nozzle and sprayed droplets meet the cold inert gas or fluid, which flows from bottom to top of the spray cooling chamber, to form spherical particles. European Patent EP0700936 describes a process for producing a solid catalyst component for olefin gas phase polymerization from a mixture of a magnesium compound with an alcohol which is sprayed in a molten state into a spray column. Simultaneously, the inside of the spray column is cooled down to a temperature at which a solid component (B) is obtained without any substantial vaporization of the alcohol in the mixture (A), to obtain the solid (B), followed by partial removal of the alcohol from the solid (B) between 20° C. and 60° C. under reduced pressure, to obtain a solid component (C).

In both cases a molten mixture is used and sprayed into a spray column containing a gas or fluid at low temperature to obtain a solid component catalyst. In this process, like the Spray-Drying process, is necessary to control many variables such as: feeding rate, gas flow to spray, flow rate of carrier gas in a chamber, temperature of the carrier gas, heated pipe for transferring the solution above 100° C., homogeneity of gas throughout the system, temperature control to maintain the gas supply, and the precipitation chamber. All these factors may lead to a more complex and expensive process.

In yet another approach, patent application WO2014095523A1 describes the use of a spray cooling technique as an alternative process to solidify a fused $Mg(OR^1)_2$ and alcohol adduct in a cold liquid, in the absence of an inert liquid dispersant. The melted mixture of $Mg(OR^1)_2$ and alcohol could be sprayed through a device in a low temperature environment to cause the solidification of particles. Thus, it suggests that the support preparation process undergoes processing under high temperature and pressure conditions.

SUMMARY OF THE INVENTION

Described herein are novel catalyst supports as well as a process of manufacture and use. Distinctions over traditional spray cooling and spray drying techniques and the differences among properties of the final catalyst support are described below.

The present invention includes a process for manufacturing a catalyst support component comprising an inorganic compound, an alcohol ROH, and an additive to increase the solubility of the inorganic compound in the alcohol ROH, comprising the steps of: a) dissolving the inorganic compound and additive in the alcohol ROH to form a solution in a reactor at or below 100° C. in an inert atmosphere at a pressure between 1 and 5 bar; b) transferring the solution to an atomizer; c) atomizing the solution to form droplets; d) contacting the droplets with a non-solvent liquid at a temperature between 10° C. and −30° C. to precipitate spherical particles; e) separating the non-solvent liquid from the spherical particles; and f) washing and drying the spherical particles to form a catalyst support.

(i) In the present invention, the temperature to prepare the solution of $MgCl_2$, additive, and alcohol is below 100° C., and from 50° C. to 70° C. in some embodiments. Contrarily, known prior art teaches values in excess of 100° C.

(ii) The present invention does not require preparation of a molten mixture, which permits the use of milder conditions. For example, the initial mixture to obtain the alcoholic solution can be prepared for about 1-3 hours in a vessel (such as Reactor A of FIG. 1 below) and under low pressure (less than 2 bar). Moreover, there is a reduction in energy consumption, as well as greater simplicity and operational safety in the overall process.

(iii) The alcoholic solution comprises an inorganic compound, an alcohol ROH, and an additive. The alcohol ROH consists of a R chosen from a C1-C18 hydrocarbon group, and the additive can be a non-polymeric, e.g., fluorine based additive.

(iv) The precipitation of solid particles occurs through the passage of said alcoholic solutions into an atomizer located inside a reactor under inert atmosphere and pressure between 1 and 2 bar. The reactor contains a non-solvent hydrocarbon at low temperature. The solution is sprayed into small droplets, which is carried to the atomizer by the controlled pressure of the inert gas applied on the alcoholic solution. This procedure has fewer variables when compared to conventional processes such as spray cooling. Further, the use of low temperature and low pressure promote much longer crystallization times to form spherical particles.

The prepared catalyst support is generally spherical and has demonstrable activity for olefin polymerization, as seen herein.

A catalyst support is prepared by a modified Spray Cooling method, comprising (a) an inorganic compound, such as a magnesium compound; (b) an alcohol ROH, wherein R can be chosen from a C1-C18 hydrocarbon group; and (c) one or more additives, such as hydrofluoroalkenes (HFAs), polyaryletherketone (PAEK) derivatives, poly(oxy-1,2-ethanediyl) derivatives, aliphatic polyether, polylactic acid and polysorbates. More specifically, the one or more additives may be: 1,1,1,2-tetrafluorethane; 1,1,1,2,3,3,3-heptafluoropentane; 1,1,1,2,2,3,4-heptafluoropentane; 1,1,1,2,2,3,4-heptafluoropentane; 1,1,3,3,4,4-hexafluorobutane; 1,1,1,2,3,4-hexafluorobutane; 1,1,1,2,2,3,3,4,4-nonafluorohexane; 1,1,1,2,2,3,3,4,5-nonafluorohexane; 1,1,1,2,2,3,3,4-octafluoropentane; 1,1,1,2,2,3,3,5-heptafluoropentane; 1,1,1,2,2,3,4,5-octafluoropentane; 1,1,1,2,2,4,4,5,5-nonafluoropentane; 1,1,1,2,3,4,4,5,5,5-decafluoropentane; sorbitan trifoliate, sorbitan monooleate, sorbitan monolaurate, polyoxyethylene sorbitan monolaurate, polyethylene sorbitan monooleate, natural lecithin, oleyl polyoxyethylene ether, stearyl polyoxyethylene ether, lauryl polyoxyethylene ether, block copolymers of oxyethylene and oxypropylene, oleic acid, synthetic lecithin, diethylene glycol dioleate, tetrahydrofurfuryl, oleate, ethyloleate, isopropyl myristate, glyceryl monooleate, glyceryl monostearate, glyceryl monoricinoleate, cetyl alcohol, polyethylene glycol, polyoxypropylene glycol, cetyl pyridinium chloride, olive oil, glyceryl monolaurate, polyoxyethylene nonyl phenolether, polyoxyetheylene monolaurate, polyethylene glycol-b-polypropylene, oleic acid polyoxyethylene dilaurate, polyoxyethylene stearyl ether, polyetheretherketone, polyetherketone, polyetherketoneketone, polyetherketoneetherketoneketone, polyetheretherketoneketone.

The amount of additive in the inorganic support obtained show at least 0.01 to 20 wt %. The catalyst support prepared has a distinct X-ray diffraction pattern and melting endotherm profile when compared to the prior art described in this document. In an embodiment of the invention, the catalyst support has at least one peak as shown by X-Ray diffraction, wherein only one peak is in the range from 0° to 10°.

Complementary melting profiles of the $MgCl_2.nEtOH$ adduct using DSC thermogram are an important parameter to distinguish the physical properties of the prepared inorganic support. Claims regarding the physical properties of supports obtained by oil emulsion technique, such as the one showed in the patent WO1998044009 (where, $MgCl_2.mROH.nH_2O$ adduct, where R is a C1-C10 alkyl, $2 \leq m \leq 4.2$, $0 \leq n \leq 0.7$), described that the thermal profile do not show peaks at temperatures below 90° C. For peaks presented below 90° C., the fusion enthalpy associated with said peaks is less than 30%. The maximum peak occurs at temperatures between 95 and 115° C. In U.S. Pat. No. 7,060,763, the $MgCl_2.mEtOH$ adduct (m=2.5 to 3.2) was characterized by a DSC profile having a single melting temperature (Tm) peak over 109° C., with an associated fusion enthalpy ($\Delta H$) of 103 J/g or lower. U.S. Pat. No. 7,087,688 claims $MgCl_2.mEtOH.nH_2O$ adduct ($3.4 < m \leq 4.4$ and $0 < n \leq 0.7$) with only one melting peak between 90-105° C. and associated fusion enthalpy lower than 125 J/g in the DSC profile.

The catalyst support of the present invention has a unique DSC profile. For example, the DSC profile can have at least a first thermal transition peak between 112° C. and 150° C. It can also have a second thermal transition peak between 181° C. and 215° C. Further still, it can have a third thermal transition peak between 235° C. and 248° C. as shown by DSC.

BRIEF DESCRIPTION OF THE DRAWINGS

Embodiments of the invention will be described by way of example with reference to the accompanying drawings.

FIG. 1 is an illustration of the apparatus used to prepare catalytic support.

FIG. 2 is a DSC thermogram of the supports SSB01 to SSB08.

FIG. 3 displays powder X-ray diffraction patterns of $MgCl_2$ and support samples SSB01 to SSB08.

FIG. 4 displays thermogravimetric analysis (TGA) of support samples SSB01 to SSB08.

FIG. 5 are images obtained by Scanning Electron Microscope (SEM).

DETAILED DESCRIPTION OF THE INVENTION

For purposes of the description hereinafter, it is to be understood that the embodiments described below may assume alternative variations and embodiments. It is also to be understood that the specific articles, compositions, and/or processes described herein are exemplary and should not be considered as limiting.

The present invention describes a catalytic support prepared using a modified Spray Cooling method. The production system is exemplified in FIG. 1, which illustrates the process steps to transfer, spray, and precipitate to obtain spherical inorganic particles used to support a ZN catalyst. The solution is first prepared in the reactor A (1). The solution is transferred through ⅛ inch tubing (2) containing a jacket to control temperature during the transfer of the solution (3). The size and shape of the droplets produced by the atomizer are controlled by the liquid pressure (4) and gas pressure—optional (5). The type of atomizer (6) is not limited and different types can be explored according to the scale and conditions of the experiment. The crystallization of the particle occurs through the contact of the droplets of alcoholic solution with the inert hydrocarbon liquid at low temperature in the reactor B (7). All steps were conducted under nitrogen or argon atmosphere. In the examples described in this invention the catalyst supports are produced using two nozzle systems: gas atomizing and hydraulic spray nozzle. In the case of using gas atomizing the atomization is produced by combination of inert gas and liquid pressures. In the case of using hydraulic spray nozzle the atomization is produced by liquid pressure.

The catalyst support produced by the modified Spray Cooling method is prepared from an alcoholic solution comprising an inorganic compound, an alcohol ROH, and an additive to increase the solubility of the inorganic compound in the alcohol ROH:

In some embodiments, the inorganic compound can be a magnesium compound (such as a magnesium halide or/and magnesium alkoxide) which can be mixed with alcohol to form a solution. The alcohol has the formula ROH, wherein R is a C1-C18 hydrocarbon group, which enables the use of a different alcohol and therefore different molar ratios. For example, the alcohol can be methanol, ethanol, propanol, iso-propanol, butanol, isobutanol, 2-ethylhexanol, chloroethanol, 2,2,2-trichloroethanol. The resulting mixture can be stirred at a temperature from 30° C. to 100° C., more specifically from 50° C. to 70° C. to form the alcoholic solution.

The inorganic compound (e.g., magnesium compounds, such as magnesium halide or/and magnesium alkoxide) is mixed with alcohol and one or more additives, in which the additives can be fluorine based compounds such as hydrofluoroalkenes (HFAs) or other compounds such as polyaryletherketone (PAEK) derivatives, poly(oxy-1,2-ethanediyl) derivatives, aliphatic polyether, polylactic acid, and polysorbates. Examples of fluorine based compounds include: 2H, 3H perfluoropentane; 1,1,1,2-tetrafluorethane; 1,1,1,2,3,3,3-heptafluoropentane; 1,1,1,2,2,3,4-heptafluoropentane; 1,1,1,2,2,3,4-heptafluorobutane; 1,1,3,3,4,4-hexafluorobutane; 1,1,1,2,3,4-hexafluorobutane; 1,1,1,2,2,3,3,4,4-nonafluorohexane; 1,1,1,2,2,3,3,4,5-nonafluorohexane; 1,1,1,2,2,3,3,4-octafluoropentane; 1,1,1,2,2,3,5-heptafluoropentane; 1,1,1,2,2,3,4,5-octafluoropentane; and 1,1,1,2,2,4,4,5,5-nonafluoropentane, 1,1,1,2,3,4,4,5,5,5-decafluoropentane. Other examples of additives include: sorbitan trifoliate, sorbitan monooleate, sorbitan monolaurate, polyoxyethylene sorbitan monolaurate, polyethylene sorbitan monooleate, natural lecithin, oleyl polyoxyethylene ether, stearyl polyoxyethylene ether, lauryl polyoxyethylene ether, block copolymers of oxyethylene and oxypropylene, oleic acid, synthetic lecithin, diethylene glycol dioleate, tetrahydrofurfuryl, oleate, ethyloleate, isopropyl myristate, glyceryl monooleate, glyceryl monostearate, glyceryl monoricinoleate, cetyl alcohol, polyethylene glycol, polyoxypropylene glycol, cetyl pyridinium chloride, olive oil, glyceryl monolaurate, polyoxyethylene nonyl phenolether, polyoxyetheylene monolaurate, polyoxyethylene dilaurate, polyoxyethylene stearyl ether, polyethylene glycol-b-polypropylene, oleic acid, polyetheretherketone, polyetherketone, polyetherketoneketone, polyetherketoneetherketoneketone, polyetheretherketoneketone. The amount of additive in the catalyst support can be between 0.01 to 20 wt %. The alcohol ROH, wherein R is a C1-C18 hydrocarbon group.

The resulting alcoholic solutions described above can be aerosolized by spraying them through a nozzle, which is placed inside the reactor, as represented in FIG. 1. The aerosolized solutions can form a precipitate when contacted with an inert liquid at low temperature, between −30° C. to 0° C. As a result, generally spherical particles are obtained, as shown in FIG. 5.

The non-solvent or inert liquid can be a aliphatic and aromatic hydrocarbon. The aliphatic hydrocarbon is selected from the group consisting of isoparaffin, hexane, heptane, octane, nonane, decane, cyclohexane or mixture of two or more hydrocarbon. The aromatic hydrocarbon is selected from benzene, toluene, xylene or the mixture of two or more hydrocarbon.

The resulting catalytic support can be subjected to a heat treatment in order to remove the excess of alcohol or additive compound or compounds. The amount of alcohol removed should correspond to a composition, in which the inorganic support obtained shows a molar ratio of at least 0.5 mol of alcohol per mol of $MgCl_2$.

The catalyst for olefin polymerization is prepared by the reaction between the catalyst support as described above with one or more titanium halides. Examples of the titanium halide include, but are not limited to, titanium tetrachloride, titanium tetrabromide, tetrabutoxy titanium, tetraethoxy titanium, tributoxy titanium chloride, dibutoxy titanium dichloride, and triethoxy titanium. Titanium halide compounds include those having chlorine (as titanium tetrachloride). The titanium halide can be used alone or in the presence of inert solvent. In some embodiments, the titanium halide component is added with an internal donor compound such as a phthalate, succinate, diether, benzoate or chemically similar compound.

Embodiments of catalyst supports described in the present application were obtained from alcoholic solutions of, comprising: (a) an inorganic compound, being a magnesium compound and (b) an inorganic compound and one or more additives through a modified spray cooling technique to form generally spherical particles having differentiated physical properties compared known catalyst supports.

Some physical properties are exemplified in FIG. 2. DSC thermograms of inventive supports SSB01 to SSB08 have endothermic peaks at three different transition temperatures. The thermal transition "A" occurs between 112° C. and 154° C.; thermal transition "B" occurs between 181° C. and 215° C.; and thermal transition "C" occurs between 235° C. and 248° C.

In order to evaluate the effect of the aerosolization method, different types of nozzles were used resulting in two different catalyst support SSB04 (example 4) and SSB05 (example 5). The sample SSB04 was obtained by the passage of the resulting alcoholic solution through a gas atomizing nozzle. The catalyst support SSB05 was produced by the hydraulic spray nozzle. The DSC thermograms show distinguishable thermal events between SSB04 and SSB05, however in both cases, the main endothermic peaks occurred at temperatures above 112° C.

In another embodiment, magnesium halide was mixed with an additive mono-(9Z)-9-octadecenoate, poly(oxy-1,2-ethanediyl) derivative (MOP) in the presence of an alcohol to obtain sample SSB06 (having 1.4 wt % of MOP Example 06), and sample SSB07 having 4.8 wt % of MOP (Example 07). As shown in FIG. 2, the addition of MOP in the initial alcoholic solution alters the endothermic peaks of the final particles.

In yet another embodiment, an alcoholic solution was prepared with $MgCl_2$, 1.3 wt % of MOP, and 28.4 wt % of fluorine based compound 1,1,1,2,3,4,4,5,5,5-decafluoropentane to produce sample SSB08 (Example 8). As shown in FIG. 2, the addition of 1,1,1,2,3,4,4,5,5,5-decafluoropentane further altered the endothermic peaks of the final particles in a solution having MOP.

The inventive examples described herein were also analyzed by X-ray diffraction analysis. As shown in FIG. 3, the diffraction patterns of the catalyst supports (SSB01-SSB08) are different for different experiment conditions and also when compared to anhydrous $MgCl_2$, which exhibits a cubic close packing structure that gives strong 2θ peaks at 15°, 35°, and 50.4°.

Examples 01 to 03 describe catalyst supports SSB01 to SSB03, respectively, and show broad diffraction features observed at around 5.6-6.1°. These results suggest the presence of an amorphous region in the obtained inorganic particle. Furthermore, comparing the results mentioned in the cited patents, the obtained inorganic particles showed additional XRD peaks with high intensity 2θ at 8.8° and 9.4° for SSB01 and 8.3° for SSB02. The support SSB03, as described in example 3, was subjected to a thermal treatment for partial elimination of alcohol and showed a different diffraction pattern without a high intensity peak below 10°. High intensity reflection below 10° characterizes alcohol interaction along the z-axis of layered structure of rhombohedral $MgCl_2$.

In order to evaluate the effect of the produced inorganic particle by different types of nozzles, samples SSB04 and SSB05 were prepared as described in the examples 4 and 5, respectively. The diffraction spectrum of these supports did not show high intensity diffraction peaks at 2θ above 10°, more specifically in between 10° and 50°. In particular, the sample SSB04 showed a single peak of greater intensity at 2θ=8.9° and a discrete peak at 2θ=9.4°. In contrast, sample SSB05 showed a single low angle peak (<10°), which was 2θ=8.3°. In the final three samples, it is important to mention that the introduction of additives aiming to improve the incorporation of $MgCl_2$ using alcohol as a solvating agent, systematically showed at least one low angle high intensity peak)(<10°. Sample SSB06, using 1.4 wt % of MOP, showed 2θ diffraction peaks at 8.9° and 9.3°. Otherwise, samples SSB07 and SSB08 showed a single crystalline 2θ peak at 8.9° and 8.4°, respectively. Therefore, samples prepared as described in example 6 to 8 showed very unique diffraction patterns. Although the additives improve the incorporation of $MgCl_2$ in alcohol, which act mainly as a solvation agent, they did not disturb crystalline adduct formation at low angle diffraction peaks. Furthermore, the results obtained in samples SSB05, SSB07, and SSB08 showed a single crystalline peak at 2θ below 10°.

Support Preparation

In some embodiments of the process to prepare a catalyst support, the catalyst support can be prepared according to steps, comprising:

Step 1: Preparation of Alcoholic Solution

To prepare a solution of inorganic compound (e.g., magnesium compound) (4 wt % to 50 wt %) by dissolving in alcohol ROH with one or more additives (5 wt % to 50 wt %), which acts as solvation agent, all the components are added to a glass reactor (FIG. 1) and the solution is prepared at temperatures below 100° C. (e.g., between 30° C. to 80° C.) under inert atmosphere (nitrogen or argon) in a stirring system using mechanical or magnetic stirrer (e.g., between 100 RPM and 600 RPM).

Step 2: Preparation of the Support

The solution is stirred under a nitrogen atmosphere, slightly pressurized (1-5 bar) at a temperature below 100° C. (e.g., between 30° C. to 80° C.). The glass reactor is then connected to a transfer line or jacketed tubing, where the temperature is equal to or slightly higher than the temperature of the alcoholic solution. The transfer line is then connected to a nozzle (e.g., an atomizer) kept inside a second reactor (e.g., reactor B of FIG. 1), which contains a non-solvent liquid at low temperature (−30° C. to 10° C.) under inert atmosphere (nitrogen or argon) slightly pressurized, which pressure is lower than a first reactor (e.g., reactor A of FIG. 1), and stirred using a mechanical stirrer (e.g., 100 RPM to 600 RPM). The alcoholic solution is transferred to the atomizer due to the higher pressure in first reactor (e.g., reactor A of FIG. 1)) and sprayed in a downward vertical direction into small droplets (See, e.g., the atomizer/nozzle in reactor B of FIG. 1), which precipitate as generally spherical particles when in contact with the non-solvent liquid at low temperature (e.g., −30° C. to 10° C.).

The resulting suspension of generally spherical particles and the non-solvent liquid is stirred (e.g., 100 RPM to 600 RPM) at low temperature (e.g., −30° C. to 10° C.) for several hours (e.g., 0.1 h to 6 h) before slowly warming the suspension to room temperature. The rate of crystallization of catalyst support depends upon residence time in the liquid medium (e.g., in Reactor B of FIG. 1) the stirring conditions (e.g., rate of rotation), and temperature, which affects the morphology and mechanical strength of the final solid particle. As a result, these conditions can produce catalyst supports with different crystalline structures.

The agitation/stirring is stopped to allow the spherical particles to settle to the bottom of the reactor. The excess non-solvent liquid is separated via cannula under inert atmosphere (e.g., nitrogen or argon) followed by the addition of excess hexane or heptane to transfer the resulting suspension to a Schlenk filter flask. Then, the non-solvents are flushed through the bottom of the flask under inert atmosphere (e.g., nitrogen or argon) retaining the generally spherical particles on the filter.

The procedure is followed by an addition of hexane or heptane, which is stirred for 30 minutes under inert atmosphere and the liquids are flushed through the bottom of the Schlenk flask. This process is repeated several times (e.g., 1 to 10 times) until the residual non-solvent is removed. The resulting spherical particles are then dried under nitrogen or argon flow for several hours (e.g., 1 h to 12 hs) to obtain the catalyst support.

Step 3: Thermal Treatment (Optional)

The spherical particles are added to or kept in a Schlenk filter flask under inert atmosphere (nitrogen or argon). The flask is placed inside an oven at initial temperature below 80° C. and under nitrogen or argon flow fluidizing the spherical support on the filter of the Schlenk flask. The thermal treatment can be carried out under isothermal conditions for several hours (e.g., 0.1 h to 12 hs) or temperature ramps can be performed up to 250° C. with ramp rates from 0.1° C./min to 100° C./min. Then, the spherical particles are cooled down to room temperature at cooling rates from 0.1° C./min to 100° C./min to obtain the catalyst support.

EXAMPLES

Example 1

A solution of $MgCl_2$ anhydride in ethanol at 4.0 wt % was prepared at room temperature. This solution was transferred through ⅛"OD jacketed tubing with controlled temperature connected to an atomizer (gas atomizer nozzle) placed inside a 5 L rounded-bottom flask to spray droplets of the alcoholic solution to dried isoparaffin at low temperature, approximately −20° C. The pressure applied in reactor A (1) and system (4) to transfer initial alcoholic solution to the atomizer was 0.7 bar, while the $N_2$ pressure (5) was 1.0 bar. The resulting suspension of the particles precipitated in isoparaffin was stirred overnight at 350 RPM. After stirring, the mixture was left for 3 hours and then the supernatant was removed and 1 L of dried hexane was added to form a suspension with the resulting particles. The resulting mixture was transferred through cannula to a Schlenk flask followed by the filtration and recovering of the particles, which was washed several times with anhydride hexane and dried under nitrogen flow. All steps of this experiment were carried out under $N_2$ atmosphere to obtain support sample SSB01.

Example 2

A solution of $MgCl_2$ anhydride in ethanol at 12.2 wt % was prepared at 60° C. This solution was transferred through ⅛"OD jacketed tubing with controlled temperature directly to a 5 L rounded-bottom flask without the use of the atomizer. The alcoholic solution was transferred to dried isoparaffin at low temperature, at approximately −20° C. The resulting suspension of the particles precipitated in isoparaffin was stirred overnight at 350 RPM. After stirring, the mixture was left for 3 hours and then the supernatant was removed and 1 L of dried hexane was added to form a suspension with the resulting particles. The resulting mixture was transferred through cannula to a Schlenk flask followed by the filtration and recovering of the particles, which was washed several times with anhydride hexane and dried under nitrogen flow. All steps of this experiment were carried out under $N_2$ atmosphere to obtain support sample SSB02.

Example 3

The support catalyst was prepared as described in Example 2, followed by an additional step to remove the excess of ethanol from the obtained particles through a thermal treatment, as follows: the support was transferred to a Schlenk filter and kept under countercurrent nitrogen flow inside an oven for 1 hour at each temperature 40° C., 50° C. and, 60° C. to obtain support SSB03.

Example 4

A solution of $MgCl_2$ anhydride in ethanol at 12.2 wt % was prepared at 60° C. This solution was transferred through ⅛"OD jacketed tubing with controlled temperature connected to an atomizer (gas atomizer nozzle) placed inside a 5 L rounded-bottom flask to spray droplets of the alcoholic solution to dried isoparaffin at low temperature, approximately −20° C. The pressure applied in reactor A (1) and system (4) to transfer initial alcoholic solution to the atomizer was 0.7 bar, while the $N_2$ pressure (5) was 1.0 bar. The resulting suspension of the particles precipitated in isoparaffin was stirred overnight at 350 RPM. After stirring, the mixture was left for 3 hours and then the supernatant was removed and 1 L of dried hexane was added to form a suspension with the resulting particles. Then, the resulting mixture was transferred through cannula to a Schlenk flask followed by the filtration and recovering of the particles, which was washed several times with anhydride hexane and dried under nitrogen flow. All steps of this experiment were carried out under $N_2$ atmosphere to obtain support sample SSB04.

Example 5

A solution of $MgCl_2$ anhydride in ethanol at 12.5 wt % was prepared at 60° C. This solution was transferred through ⅛"OD jacketed tubing with controlled temperature connected to an atomizer (hydraulic spray nozzle) and placed inside a 5 L rounded-bottom flask to spray droplets of the alcoholic solution to dried isoparaffin at low temperature, approximately −20° C. The pressured applied in reactor A (1) and system (4) to transfer initial alcoholic solution to the atomizer was 1.0 bar. The resulting suspension of the particles precipitated in isoparaffin was stirred overnight at 350 RPM. After stopping the stirring, the mixture was left for 3 hours and then the supernatant was removed and 1 L of dried hexane was added to form a suspension with the resulting particles. Then, the resulting mixture was transferred through cannula to a Schlenk flask followed by the filtration and recovering of the particles, which was washed several times with anhydride hexane and dried under nitrogen flow. All steps of this experiment were carried out under $N_2$ atmosphere to obtain support sample SSB05.

Example 6

A solution of $MgCl_2$ anhydride in ethanol at 15.6 wt % was prepared at 60° C. In this solution was added 1.4 wt % of MOP and then transferred through ⅛"OD jacketed tubing with controlled temperature connected to an atomizer (hydraulic spray nozzle) placed inside a 5 L rounded-bottom flask to spray droplets of the alcoholic solution to dried isoparaffin at low temperature, approximately −20° C. The pressure applied in reactor A (1) and system (4) to transfer initial alcoholic solution to the atomizer was 1.0 bar. The resulting suspension of the particles precipitated in isoparaffin was stirred overnight at 350 RPM. After stopping the stirring, the mixture was left for 3 hours and then the supernatant was removed and 1 L of dried hexane was added to form a suspension with the resulting particles. Then, the resulting mixture was transferred through cannula to a Schlenk flask followed by the filtration and recovering of the particles, which was washed several times with anhydride hexane and dried under nitrogen flow. All steps of this experiment were carried out under $N_2$ atmosphere to obtain support sample SSB06.

Example 7

A solution of $MgCl_2$ anhydride in ethanol at 18.0 wt % was prepared at 60° C. In this solution was added 4.8 wt % of MOP and then transferred through ⅛"OD jacketed tubing with controlled temperature connected to an atomizer (hydraulic spray nozzle) placed inside a 5 L rounded-bottom flask to spray droplets of the alcoholic solution to dried isoparaffin at low temperature, approximately −20° C. The pressured applied in reactor A (1) and system (4) to transfer initial alcoholic solution to the atomizer was 1.0 bar. The resulting suspension of the particles precipitated in isoparaffin was stirred overnight at 350 rpm. After stirring, the mixture was left for 3 hours and then the supernatant was removed and 1 L of dried hexane was added to form a suspension with the resulting particles. The resulting mixture was transferred through cannula to a Schlenk flask followed by the filtration and recovering of the particles, which was washed several times with anhydride hexane and dried under nitrogen flow. All steps of this experiment were carried out under $N_2$ atmosphere to obtain support sample SSB07.

Example 8

A solution of $MgCl_2$ anhydride in ethanol at 15.6 wt % was prepared at 70° C. In this solution was added 1.3 wt % of MOP and 28.4 wt % of 1,1,1,2,3,4,4,5,5,5-decafluoropentane. The resulting solution was transferred through ⅛"OD jacketed tubing with controlled temperature connected to an atomizer (hydraulic spray nozzle) placed inside a 5 L rounded-bottom flask to spray droplets of the alcoholic solution to dried isoparaffin at low temperature, approximately −20° C. The pressure applied in reactor A (1) and system (4) to transfer initial alcoholic solution to the atomizer was 1.0 bar. The resulting suspension of the particles precipitated in isoparaffin was stirred overnight at 350 RPM. After stirring, the mixture was left for 3 hours and then the supernatant was removed and 1 L of dried hexane was added to form a suspension with the resulting particles. The resulting mixture was transferred through cannula to a Schlenk flask followed by the filtration and recovering of the particles, which was washed several times with anhydride hexane and dried under nitrogen flow. All steps of this experiment were carried out under $N_2$ atmosphere to obtain support sample SSB08.

Catalyst Synthesis

Example 9

To a 300 mL Schlenk flask equipped with a sealed mechanical stirrer under $N_2$ atmosphere, 100 ml of $TiCl_4$ was added and the temperature was cooled down to 0° C. Then, 5.7 g of support (obtained from example 1 to 8) was added and the mixture was stirred at 350 RPM followed by the dropwise addition of 22 ml of diisobutyl phthalate in hexane 10 wt %. The temperature of the reactive mixture was increased to 100° C. and stirred for 1 hour. The unreacted $TiCl_4$ and its residues were removed by filtration followed by an additional 100 ml of $TiCl_4$ to remove undesired remain residues. Thus, the resulting suspension was stirred for 1 hour at 120° C. and filtered again. The solid catalyst was washed several times with anhydride hexane at 60° C. and dried under $N_2$ to obtain catalysts SCB01 to SCB08, except for SCB05, which support sample SSB05 was contaminated during the experiment. All residual $TiCl_4$ was quenched with ethanol/hexane mixture.

Polymerization of Propylene

Example 10

Propylene polymerizations were performance in bulk using a 3.8 L stainless-steel reactor equipped with a mechanical stirrer, a manometer, a temperature indicator, a system for feeding the catalyst, monomer supply line, and a jacket for thermostatic temperature control. First, in a flask under $N_2$ atmosphere, 10 mg of catalyst was dispersed in 70 ml of hexane and then hexane solutions of triethyl aluminium 10 wt % and cyclohexylmethyl-dimethoxysilane 5 wt % were added. The pre-contact was left under stirring for 10 minutes. For propylene polymerization, the reactor was purged with nitrogen flow at 70° C. for 1 hour; then the catalyst dispersion was introduced into the reactor under $N_2$ flow at 30° C. Hereafter, $H_2$ (1 bar) and 2.3 kg of liquid propylene were fed under stirring. The temperature was raised to 70° C. and the polymerization was carried under this condition for 2 hours. The unreacted propylene was flashed off and the resulting polymers SCB01-PP to SCB08-PP were recovered and dried at 70° C. under vacuum.

The application of the catalyst system of the present study is not limited by propylene polymerization. It can be applied in polymerization of other olefins.

Characterization

The obtained supports were characterized by atomic absorption spectrometry analysis (AA) by Spectra A 50B Varian, potentiometric titration was carried out in a 808 Titrando Metrohm and Ultraviolet-visible spectrophotometry (UV-vis) in a Cary 100 Conc. Varian to quantify Mg (%), Cl (%); For thermal properties an evaluation sample was prepared in aluminum pans under nitrogen atmosphere to avoid exposure to moisture and analyzed by a differential scanning calorimeter (DSC) TA instrument, at a scanning rate of 10° C./min in the range 25° C. to 300° C. The samples were characterized by a Rigaku D/Max 2100 Powder X-ray Diffractometer Cu K☐ radiation (☐=1.5405 Å) with a diffracted beam graphite monochromator. Scanning electron microscope (SEM) images were performed using TM1000—Hitach (Low Vacuum). Support and catalyst average particle size and particle size distribution were carried out by a laser light diffraction method using Apparatus Master Sizer Hydro 2000S from Malvern.

The resulting polypropylene xylenes solubles (XS) were measured according to standard ASTM D 5492-06. Pentad analyses were carried out by $^{13}C$ NMR spectrum in an Agilent 500 MHz at 120° C. in TCE-d/ODCB-d (1:1 v/v) equipped with a 5 mm probe. Gel permeation chromatography (GPC) was carried out on Alliance GPC 2000 from Waters using TCB as a solvent at 140° C. after calibration with standard polystyrene samples. Polymer powder measurements were carried out according to ASTM D 1921-06.

TABLE 1

Elementary analysis of catalyst support

| Support | (Mg) (%) | Cl (%) |
|---|---|---|
| SSB01 | 7.4 | 28.7 |
| SSB02 | 8.6 | 35.7 |
| SSB03 | 10.3 | 41.8 |
| SSB04 | 8.0 | 29.7 |
| SSB05 | 11.7 | 37.1 |
| SSB06 | 8.8 | 56.0 |
| SSB07 | 7.8 | 46.7 |
| SSB08 | 7.3 | 22.1 |

TABLE 2

Elementary analysis of catalyst

| Catalyst[a] | (Mg) (%) | Cl (%) | Ti (%) |
|---|---|---|---|
| SCB01 | 16.2 | 58.6 | 5.8 |
| SCB02 | 13.8 | 58.9 | 6.4 |
| SCB03 | 14.6 | 58.4 | 5.3 |
| SCB04 | 13.3 | 55.1 | 5.6 |
| SCB05[b] | NA | NA | NA |
| SCB06 | 13.3 | 56.0 | 6.9 |
| SCB07 | 6.3 | 45.7 | 11.4 |
| SCB08 | 7.6 | 42.4 | 10.4 |

[a]Catalysts SCB01 to SCB08 were prepared from their correspondent supports number SSB01 to SSB08.
[b]The support SSB05 was not used to prepare catalyst.

TABLE 3

Average particle diameter and Span

| Catalyst[a] | D50 (μm) | Span |
|---|---|---|
| SCB01 | 24 | 2.8 |
| SCB02 | 90 | 2.0 |
| SCB03 | 122 | 1.9 |
| SCB04 | 45 | 2.8 |
| SCB05 | NA | NA |
| SCB06 | 72 | 1.8 |
| SCB07 | 50 | 2.4 |
| SCB08 | 54 | 2.3 |

[a]Catalysts SCB01 to SCB08 were prepared from their correspondent supports number SSB01 to SSB08, except from support SSB05 which was not used to prepare catalyst.

TABLE 4

Catalyst performance and their correspondent polymers properties of SCB01-PP to SCB08-PP.

| Polymers | Activity (kg/g) | XS[a] (%) | MFI | MWD[b] | mmmm[c] (mol %) | % powder[e] <0.1 mm |
|---|---|---|---|---|---|---|
| SCB01-PP | 6 | 8.4 | 14.3 | 4.2 | 90.6 | NA |
| SCB02-PP | 30 | 5.7 | 11.7 | 3.7 | 92.5 | 0.4 |
| SCB03-PP | 24 | 4.8 | 17.9 | 4.1 | 88.8 | 1.4 |
| SCB04-PP | 32 | 3.6 | 11.7 | 3.7 | 93.1 | 1.1 |
| SCB05-PP[d] | NA | NA | NA | NA | NA | NA |
| SCB06-PP | 40 | 4.1 | 10.6 | 6.1 | 94.0 | 0.1 |
| SCB07-PP | 12 | 4.5 | 24.8 | 7.1 | 93.0 | 0.6 |
| SCB08-PP | 10 | 4.3 | 23.8 | 7.1 | 93.1 | 1.5 |

[a]Wet method;
[b]determined with GPC;
[c]determined with $^{13}$C NMR;
[d]SCB05 was not prepared;
[e]samples with activity below 10 kg of PP/g of catalyst were not measured.

What is claimed is:

1. A catalyst support component comprising an inorganic compound, an alcohol ROH, and an additive, wherein the catalyst support component has a first thermal transition peak between 112° C. and 150° C. as shown by DSC, and at least one peak as shown by X-Ray diffraction, wherein only one peak is in the range from 0° to 10°.

2. The catalyst support component of claim 1, wherein the alcohol ROH consists of a R chosen from a C1-C18 hydrocarbon group.

3. The catalyst support component of claim 1, wherein the additive is a non-polymeric additive.

4. The catalyst support component of claim 3, wherein the non-polymeric additive is a fluorine-based additive.

5. The catalyst support component of claim 1, wherein the additive is selected from one or more of hydrofluoroalkenes (HFAs), polyaryletherketone (PAEK) derivatives, poly(oxy-1,2-ethanediyl) derivatives, aliphatic polyethers, polylactic acid, or polysorbates.

6. The catalyst support component of claim 4, wherein the additive is fluorine-based and selected from the group consisting of perfluoropentane; 1,1,1,2-tetrafluorethane; 1,1,1,2,3,3,3-heptafluoropentane; 1,1,1,2,2,3,4-heptafluoropentane; 1,1,1,2,2,3,4-heptafluorobutane; 1,1,3,3,4,4-hexafluorobutane; 1,1,1,2,3,4-hexafluorobutane; 1,1,1,2,2,3,3,4,4-nonafluorohexane; 1,1,1,2,2,3,3,4,5-nonafluorohexane; 1,1,1,2,2,3,3,4-octafluoropentane; 1,1,1,2,2,3,5-heptafluoropentane; 1,1,1,2,2,3,4,5-octafluoropentane; 1,1,1,2,2,4,4,5,5-nonafluoropentane, and 1,1,1,2,3,4,4,5,5,5-decafluoropentane.

7. A process for the polymerization of olefins comprising contacting a monomer with an activated catalyst produced with the catalyst support component of claim 4.

* * * * *